United States Patent [19]

Seago

[11] Patent Number: 4,604,182
[45] Date of Patent: Aug. 5, 1986

[54] PERFLUOROSULFONIC ACID POLYMER-COATED INDICATOR ELECTRODES

[75] Inventor: James L. Seago, Bear, Del.

[73] Assignee: E. I. Du Pont de Nemours and Company, Wilmington, Del.

[21] Appl. No.: 696,196

[22] Filed: Jan. 29, 1985

Related U.S. Application Data

[62] Division of Ser. No. 523,168, Aug. 15, 1983, Pat. No. 4,517,291.

[51] Int. Cl.⁴ .............................................. C12Q 1/54
[52] U.S. Cl. ................................... 204/403; 204/415; 435/288; 435/291
[58] Field of Search ............... 204/1 E, 1 T, 403, 415, 204/418; 435/288, 291

[56] References Cited

U.S. PATENT DOCUMENTS

| | | | |
|---|---|---|---|
| 3,707,455 | 12/1972 | Derr et al. | 204/415 |
| 3,770,607 | 11/1973 | Williams | 204/403 |
| 3,902,970 | 9/1975 | Levin | 204/1 E |
| 3,911,901 | 10/1975 | Niedrach et al. | 204/403 |
| 3,912,614 | 10/1975 | Spracklen et al. | 204/403 |
| 3,917,451 | 11/1975 | Groves et al. | 204/403 |
| 3,966,580 | 6/1976 | Janata et al. | 204/403 |
| 4,256,561 | 3/1981 | Schindler et al. | 204/418 |
| 4,260,680 | 4/1981 | Muramatsu et al. | 204/1 E |
| 4,299,919 | 11/1981 | Jellinek | 204/403 |
| 4,317,879 | 3/1982 | Busby et al. | 204/403 |
| 4,331,767 | 5/1982 | Nakajima et al. | 435/291 |
| 4,340,457 | 7/1982 | Kater | 204/403 |
| 4,399,002 | 8/1983 | Freiser et al. | 204/418 |
| 4,455,370 | 6/1984 | Bartelsman et al. | 204/403 |

OTHER PUBLICATIONS

Inman et al, "The Immobilization of Enzymes on Nylon Structures and Their Use in Automated Analysis", 1972.

*Primary Examiner*—John F. Niebling
*Assistant Examiner*—Terryence Chapman

[57] ABSTRACT

A method is described for the amperometric determination of the concentration in a biological sample of a constituent which is a substrate for an oxidase enzyme by (1) catalyzing the substrate with the enzyme, thereby consuming $O_2$ and producing $H_2O_2$ and (2) measuring the $O_2$ consumption or $H_2O_2$ production by means of an inert metal indicator electrode intimately coated with a thin film of a perfluorosulfonic acid polymer.

A reaction chamber is described which provides means for contacting the sample with the enzyme and means for making amperometric measurements utilizing inert metal indicator electrodes coated with a thin film of a perfluorosulfonic acid polymer.

11 Claims, 1 Drawing Figure

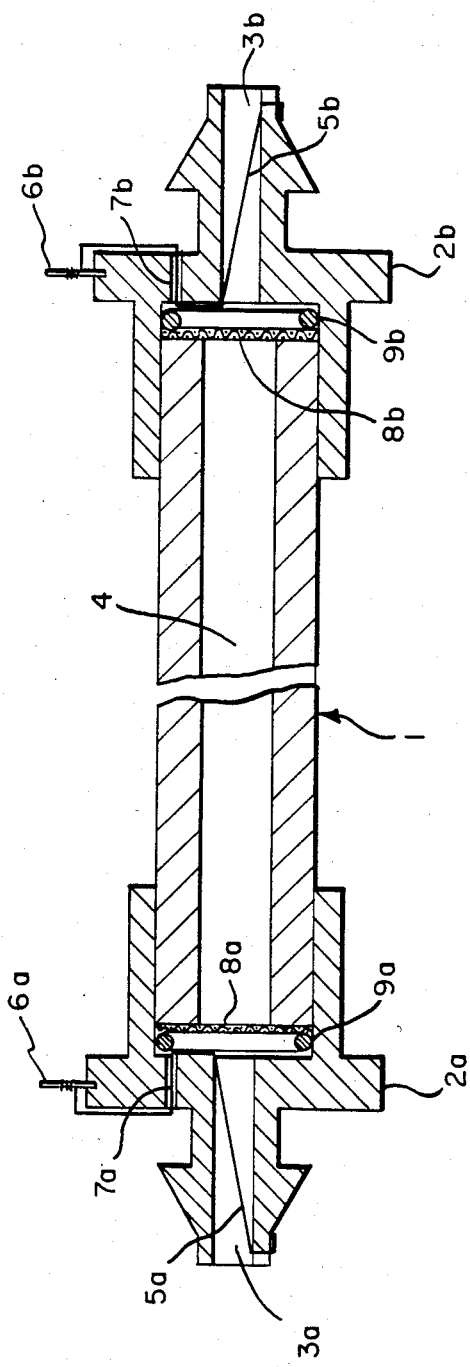

PERFLUOROSULFONIC ACID POLYMER-COATED INDICATOR ELECTRODES

This is a division of application Ser. No. 523,168 filed Aug. 15, 1983 now U.S. Pat. No. 4,517,291.

BACKGROUND ART

Amperometric methods for the detection and quantification of constituents in biological samples are known. These methods comprise the following steps:
 (1) contacting said constituent with an oxidase enzyme for which the constituent is a substrate, thereby producing a change in the concentration of an electroactive substance in said sample;
 (2) contacting said sample containing said electroactive substance with an inert metal indicator electrode;
 (3) measuring the current flow between said indicator electrode and a counter electrode at a preselected potential difference between said electrodes; and
 (4) relating the current to the concentration of the constituent initially present in the biological sample.

A recognized problem associated with such methods is the fouling of the indicator (also referred to as sensor) electrode by macromolecules which are found in biological test samples. The art has seen the development of numerous designs to circumvent this problem.

U.S. Pat. No. 3,539,455 issued to Clark on Nov. 10, 1970, discloses an electrode system suitable for the amperometric (or polarographic) determination of simple sugars which are, themselves, not electrochemically active. In a preferred embodiment, a polarographically active anode (e.g., platinum) is separated from a test solution by a semi-permeable membrane through which glucose can pass but through which large molecules, especially enzymes, cannot pass. Between the membrane and the anode surface is an enzyme such as glucose oxidase. When the glucose diffuses through the membrane, it reacts with glucose oxidase to produce hydrogen peroxide which depolarizes the anode thereby generating a measurable current in associated electronics. The semi-permeable membrane not only serves to keep glucose oxidase from diffusing out into the test solution, but also serves to prevent the enzyme catalase (which catalyzes the breakdown of hydrogen peroxide into a nonelectroactive species) from diffusing into the enzyme-containing volume.

U.S. Pat. No. 3,912,614 issued to Sprachlen et al. on Oct. 14, 1975, discusses the use of platinum electrodes for amperometric measurements of constituents found in biological samples, as well as the limitations on the use of platinum for this purpose, e.g., poisoning. According to Sprachlen et al., the use of noble metal electrodes covered with membranes permeable to the constituent to be measured, such as those membranes taught by Clark, are not entirely satisfactory, partly because of the diffusion characteristics of the membrane materials relied upon by Clark and partly because of the lack of structural integrity of such materials when exposed to air, e.g., cracking and inability to rehydrate satisfactorily.

To circumvent these problems, Sprachlen et al. developed reversible membranes (ones which could be dried and rehydrated without loss of structural integrity). Sprachlen et al. departed from the thin films of the prior art and used, instead, thick films which were hemispheric in the area of diffusion. Sprachlen et al. used hydrophilic polymers in either thick or thin films although the former were preferred because of the surprising result that the diffusion rate of oxygen (a constituent of interest) increased as the thickness of the membrane increased—up to a point. When the thickness exceeded a certain value, the diffusion rate began to fall. Sprachlen et al. found that optimum membrane thickness was about 2 to 3.5 times that of the electrode diameter.

U.S. Pat. No. 4,041,933 issued to Reichenberger on Aug. 16, 1977, discloses a polarographic electrode for measuring constituents in physiological media. A noble metal cathode within an insulating sheath has one end exposed to the test solution. This end is covered with an oxygen permeable membrane, generally a hydrophilic material such as polymethacrylate, polystyrol or cellulose acetate.

Certain uses of perfluorosulfonic acid polymers in electrode systems have been described. Perfluorosulfonic acid polymers are available commercially from the Du Pont Company as the product sold under the trademark "Nafion".

U.S. Pat. No. 4,265,714 issued to Nolan et al. on May 5, 1981, discloses a gas detecting device utilizing a hydrated, solid polymer electrolyte ion transporting membrane in electrical contact with an improved catalytic graphite sensing electrode in conjunction with reference and counter electrodes. Among other things, the solid polymer electrolyte ion transporting membrane can be a hydrated copolymer of polytetrafluoroethylene and polysulfonyl fluoride vinyl ether containing pendant sulfonic acid groups.

Martin & Freiser, Anal. Chem., Volume 53, p 902 (1981), describe the use of perfluorosulfonate cation-exchange polymers in potentiometric, ion-selective electrodes.

Cajn et al., Anal. Chem., Volume 51, 1323 (1979), characterize previous thin layer electrode designs as expensive, difficult to construct and requiring unusual manipulative techniques. These workers describe a simple and inexpensive wire thin layer electrode and cell system for potentiometric measurements. The cell consists of an outside cylinder of Teflon ® tubing containing a thin layer electrode assembly, a reference electrode and an auxiliary electrode. The thin layer electrode assembly consists of a gold wire surrounded by Nafion ® membrane tubing. There is a space between the gold wire surface and the Nafion ® membrane which serves as a thin layer cavity which contains the electrolysis solution. The reference electrode is also made with Nafion ®.

Rubinstein and Bard, J. Amer. Chem. Soc., Volume 103, 5007 (1981) describe electrodes made from Nafion ® coated pyrolitic graphite, glassy carbon or platinum. The Nafion ® was used as a matrix for the incorporation of an electroactive catalyst to form a chemically modified electrode surface. These investigators measured the chemiluminescence resulting from the interaction of the electroactive catalyst with oxalate ions in a test solution and demonstrated electrochemical regeneration of the catalyst.

From the review of the patents and literature references discussed above, it can be seen that many designs have been formulated to prevent fouling of indicator electrodes in the amperometric determination of constituents in biological samples. As some of these references themselves point out, many of these designs are difficult and expensive to construct or require careful adjustment of membrane thickness. Many have response times which are slower than that of a bare indicator electrode because of inherent design limitations on diffusion of electroactive species or constituent of interest to the electrode surface. Accordingly, there is a need for a simple, rapidly responsive, inexpensive indicator electrode useful for the amperometric determination of constituents in biological samples, particularly for constituents which are not electroactive but which are substrates for oxidase enzymes which can catalyze the breakdown of the constituent into an electroactive substance.

DISCLOSURE OF THE INVENTION

In a first aspect, the present invention is the use of an inert metal electrode having an intimate coating thereon of a thin film of a perfluorosulfonic acid polymer as an indicator electrode in amperometric methods already known in the art.

In a second aspect, the present invention is a flow-through enzyme reactor utilizing the polymer-coated electrodes for the amperometric determination of a constituent of interest contained in a liquid sample, comprising:

a first and a second end member, each having an internal chamber communicable with a source and a sink, respectively, of said liquid sample, said first and second chambers each having disposed therein a noble metal wire having coated thereon a thin film of a perfluorosulfonic acid polymer, said wires being externally connectable to electronic circuitry, said end members being made from an insulating material; and a central member having an internal chamber adapted to contain an immobilized oxidase enzyme, said chamber in communication with said internal chambers of said end members, said central chamber being separated from each of said end chambers by a foraminous septum, said septum being capable of containing the immobilized enzyme within the central chamber, said central chamber being made from an inert, conductive material.

BRIEF DESCRIPTION OF THE DRAWING

The figure is a side elevational view entirely in section of the flow-through reaction chamber which embodies the second aspect of this invention.

DETAILED DESCRIPTION OF THE INVENTION

An inert metal indicator electrode in accordance with the first aspect of the present invention is made by dip coating an inert metal, generally in the form of a thin wire, into a solution of a perfluorosulfonic acid polymer in a lower aliphatic alcohol. Preferred metals are noble metals, particularly platinum and gold, the former being most preferred because of its inherent strength and ability to be soldered directly to electrical contact posts or leads. Platinum wire as thin as 38 gauge has been used successfully. Perfluorosulfonic acid polymers having equivalent weights (ew) of at least 900 can be used but equivalent weights of at least 1100 are preferred. Polymer solutions can be prepared by following the procedure described by Martin et al. in Anal. Chem., Volume 54, 1639 (1982). These workers found that both 50:50 propanol-water and 50:50 ethanol-water, when heated to 250° C. in a high pressure reactor, will dissolve both the 1100 and the 1200 ew Nafion ®. A typical procedure for preparation of a 1% (wt/vol) solution of the polymer is as follows. A sheet of the commercial polymer is placed in a beaker containing the solvent, and this is placed in an ultrasonic cleaner for 1 h. This procedure, while not necessary to the dissolution process, appears to rid the polymer of a suspected impurity in that the commercial polymer has a yellow tinge, but is totally colorless after this treatment. The polymer sheet is then placed in a high pressure reactor with 100 mL of the solvent. The reactor is sealed and purged with nitrogen. A stirrer is turned on and the temperature raised to 250° C. The temperature is held at 250° C. for 1 h, after which the heater is turned off and the reactor is allowed to cool. After cooling, the 1% solution is removed from the reactor. The 1% solution can be concentrated by solvent evaporation. The inert metal is then dip coated in the perfluorosulfonic acid polymer solution. The alcohol is allowed to evaporate after which a powdery coating is left on the inert metal surface. Finally, the powdery coating is sintered by heating to 150° C. in an air oven to produce a smooth polymer coating. This process leaves a thin film of polymer, generally less than 0.001". Films as thick as 0.005" can be used, but thicknesses of less than 0.001" are preferred.

The electrode made as described above can be used as the indicator electrode in conventional amperometric techniques. A preferred use is in measuring the concentration of a nonelectroactive constituent such as glucose, the reaction of which with glucose oxidase yields hydrogen peroxide and consumes oxygen, both of which are electroactive. Other nonelectroactive constituents and suitable enzymes for their catalysis are disclosed in U.S. Pat. No. 3,539,455 which is incorporated herein by reference.

In one embodiment, the indicator electrode made as described above, and a counter electrode which is, in general, a nonpolarized, large inert conductive surface, are inserted into a vessel containing the test solution containing the constituent of interest and a nonrate-limiting amount of the oxidase enzyme specific for its catalysis. A preselected potential difference is impressed across the two electrodes. This potential difference and its direction are a function of the electroactive species sought to be measured. The potential difference must be such that it is sufficient to cause an electrochemical reaction at the indicator electrode in a manner which is dependent upon the concentration of the electroactive species generated or consumed by the enzymatic catalysis of the constituent of interest. It is preferable to set the potential difference at a magnitude which avoids interference by nonenzymatically generated electroactive species.

The magnitude and direction of the potential difference can be determined empirically or from published polarographic data.

For the measurement of oxygen, the potential will be in the range of 0.6 to 0.8 volts, negative on the indicator electrode. For the measurement of hydrogen peroxide, the potential will be in the range of 0.4 to 0.8 volts, positive on the indicator electrode.

The preferred mode of using the indicator electrode of this invention in amperometric methods is in a flow-through or stop-flow reaction chamber having the enzyme of interest contained therein. This chamber constitutes the second aspect of this invention. One indicator electrode is in contact with the test sample at the entrance of the reaction chamber. A background current reflecting the concentration of interfering electroactive substances is measured. The solution is then caused to enter the reaction chamber where the enzyme catalyzes the breakdown of the constituent of interest thereby consuming oxygen and producing hydrogen peroxide. A second indicator electrode of substantially the same configuration as the first, located at the exit of the reaction chamber, is then used to make a second measurement which reflects the sum of the concentration of the constituent of interest and the concentration of interfering electroactive substances. In a preferred embodiment, a substantially equal length of each electrode wire is exposed to the test sample. The currents measured by each indicator electrode may be scaled so that the difference between the currents will reflect only the concentration of the constituent of interest. The reaction chamber can be made of various forms of carbon, in which case the chamber itself can also function as the counter electrode. Suitable forms of carbon are graphite, wax or polymer-filled graphites, glassy carbon, and pyrolitic graphite. Glassy carbon is preferred because it is nonporous and highly conductive.

The flow-through reaction chamber which embodies the second aspect of this invention is described with reference to the accompanying drawing which is a side elevational view entirely in section of the reaction chamber.

The reaction chamber generally indicated by the Figure includes a central member generally in the form of a hollow cylinder (1) supported at each end between first and second end members or fittings (2a) and (2b). The fittings are generally made of an insulating material such as plastic. Each fitting has an internal chamber or port (3a) and (3b), respectively, therein. The ports communicate with a central internal chamber (4) disposed within the cylinder (1).

The test solution enters through the entrance port (3a) where it comes into contact with a first perfluorosulfonic acid polymer-coated noble metal wire (5a) which serves as an indicator electrode as described previously. The wire is electrically connected to a first external terminal (6a) and configured such that it enters the interior of the reactor through a small aperture (7a) which is then sealed. The wire is positioned within the entrance port (3a) to cross the entire sample stream and pulled outside the port where it is fastened securely to the exterior of the fitting. The solution then passes across a first foraminous septum (8a) which is held in place between a first O ring (9a) and the end face of the central cylinder (1). The central internal chamber (4) of the central cylinder (1) contains the enzyme of interest immobilized on a solid support. The solution then passes across a second foraminous septum (8b) held in place between a second O ring (9b) as described previously for septum (8a). The solution then passes through the exit port (3b) disposed within the second end fitting containing a second perfluorosulfonic acid polymer-coated noble metal wire (5b) disposed within the port (3b) in a manner substantially identical to that in which the wire (5a) is disposed within fitting (2a). The second wire is connected to a second external terminal (6b). The second wire also serves as an indicator electrode. A voltage suitable for making the desired amperometric determination is impressed across each indicator electrode and the central cylinder which, in a preferred embodiment, can be made of carbon in which case it serves as the counter electrode. The currents flowing between the counter electrode and the entrance and exit electrodes are measured. The entrance electrode current which reflects interfering electroactive substances (background) is subtracted from the exit electrode current which reflects the sum of background plus enzyme-generated current.

The following examples illustrate the invention.

EXAMPLE

A. Preparation of Nafion ® Coated Wire Electrode

A section of 38 gauge platinum wire was cleaned and degreased and slowly immersed in a 10% solution of Nafion ® (1,100 eq. wt.) in n-propanol for 30 seconds, rotating the wire to free any entrapped air bubbles. The wire was then slowly withdrawn so as to provide an even coating of polymer. The excess coating was removed by a rapid arm swing. The coated wire was allowed to air dry for 3-5 minutes (thin white powder visible) and then placed in a pre-heated oven (150° C.) from 30 to 120 minutes to sinter the coating. The coated wire was ready to use at this point, but could be stored dry in air or in buffer solution. Due to the thin film of polymer (0.001") rapid hydration and ionic equilibration will occur in the buffer solution.

B. Flow-Through Enzyme Reaction Chamber

Both the entrance and exit electrodes, made from a section of Nafion ® coated wire, were mounted in barbed nylon pipe fittings (Valve Plastics #1810-1) serving as end members. One end of each Nafion ®-coated wire was secured in a slit (approx. 1/16") in each fitting and sealed. The wire was then threaded through and across the sample stream (port) and out of an aperture (0.028" dia) drilled in each fitting which was then sealed with RTV silicone rubber. The other end of the wire was soldered to a contact pin (0.025" square wire wrap header post). An O ring was inserted into the larger opening of the fitting to electrically insulate each sensor electrode from the graphite counter electrode and to provide additional sealing against air leaks from the aperture through which the sensor wire penetrates the fitting. A circular support of nylon mesh serving as a foraminous septum (88 mesh, 0.220" dia - Small Parts P/N CMN-88) was inserted between the O ring and the end face of the hollow graphite reactor column. The graphite reactor column, serving also as the counter electrode (Alpha Chemical - P/N 00891), was turned down to a suitable outside diameter (0.215") for a snug friction fit into each plastic fitting. The graphite column had an inner diameter of 0.062" and a length of about 1". Silicone vacuum grease was applied to the outer surface to seal the porous graphite against air leaks.

Glucose oxidase was covalently linked to amino derivatized controlled pore glass beads using glutaraldehyde. The beads were slurry packed into the graphite reactor column with a vacuum to draw off the excess water and help settle the bed. Then the second nylon mesh bed support was placed over the open end of the column, and the second detector with the O ring in place was press fitted over the graphite reactor column. The assembly was tested for air leaks and fluid flow.

The detector assembly made as described above was connected to associated electronics. The electronics were used to maintain a constant potential between the sensing electrodes and the counter electrode and to measure the current flow between each sensor electrode and the counter electrode. The current flow was converted into a voltage which was amplified and processed. The common graphite counter electrode was driven negative with respect to the indicator electrodes both of which were maintained at OV or ground potential. Response curves were obtained for each of the two sensor electrodes by passing through the detector assembly a stream of an aqueous phosphate buffer at a flow rate of 1 mL/min into which 4 microliter samples containing varying amounts of hydrogen peroxide were injected once every 30 seconds. Peroxide concentrations ranged from 50 $\mu$M to 500 $\mu$M. The currents flowing between each sensing electrode were scaled using associated electronics so that the two currents were substantially the same. The response of each sensing electrode had peaked and returned to baseline within thirty seconds. Peak response was obtained within three to ten seconds.

Next, four microliters of a 1:10 dilution of glucose standards containing between 10 and 500 mg/dL were injected into the buffer stream every thirty seconds. The sensor at the entrance port of the detector showed no response, while the sensor at the exit port of the detector showed a response whose peak height and area varied linearly over the entire glucose range. The response peaked and returned to baseline within thirty seconds.

Serum samples were also introduced into the buffer stream in the same manner. The sensor at the entrance port detected interfering components in the serum. The sensor at the exit port detected enzymatically generated $H_2O_2$, as well as interfering components. The difference between the responses of the two sensing electrodes was compared to a standard curve to calculate the concentration of glucose in the serum sample. The calculated value of glucose compared favorably with values obtained by independent chemical analyses.

I claim:

1. A flow-through enzyme reactor for the amperometric determination of a constituent of interest contained in a liquid sample, comprising:

a first and a second end member, each having an internal chamber communicable with a source and a sink, respectively, of said liquid sample, said first and second chambers each having disposed therein a noble metal wire having coated thereon a thin film of a perfluorosulfonic acid polymer, said wires being externally connectable to electronic circuitry, said end members being made from an insulating material; and a central member having an internal chamber adapted to contain an immobilized oxidase enzyme, said chamber in communication with said internal chambers of said end members, said central chamber being separated from each of said end chambers by a foraminous septum, said septum being capable of containing the immobilized enzyme within the central chamber, said central chamber being made from an inert, electrically conductive material.

2. The reactor of claim 1 wherein the noble metal wire is selected from the group consisting of platinum and gold.

3. The reactor of claim 2 wherein the noble metal wire is platinum.

4. The reactor of claim 1 wherein the thin film is less than about 0.005 inch.

5. The reactor of claim 1 wherein the thin film is about 0.001 inch.

6. The reactor of claim 1 wherein the perfluorosulfonic acid polymer has an equivalent weight of at least about 900.

7. The reactor of claim 6 wherein the perfluorosulfonic acid polymer has an equivalent weight of about 1100.

8. The reactor of claim 1 wherein the central member is made from an inert conductive material selected from the group consisting of graphite, wax-filled graphite, polymer-filled graphite, pyrolitic graphite and glassy carbon.

9. The reactor of claim 8 wherein the inert conductive material is glassy carbon.

10. The reactor of claim 1 wherein the noble metal wire is about 38 gauge.

11. The reactor of claim 1 wherein the foraminous septum is a nylon mesh.

* * * * *